United States Patent [19]

Stewart et al.

[11] Patent Number: 4,492,639

[45] Date of Patent: Jan. 8, 1985

[54] LEAK DETECTION

[75] Inventors: Thomas L. Stewart, Houston; Florian C. Demny, Pasadena, both of Tex.

[73] Assignee: Shell Oil Company, Houston, Tex.

[21] Appl. No.: 582,416

[22] Filed: Feb. 22, 1984

[51] Int. Cl.³ .................... B01D 17/02; B01D 33/00
[52] U.S. Cl. .................................. 210/746; 210/781; 210/96.1; 210/103; 73/61.1 R
[58] Field of Search ............... 210/636, 742, 746, 773, 210/774, 781, 96.1, 97, 103; 73/61.1 R; 184/1 B, 5, 6.24, 81, 100

[56] References Cited

U.S. PATENT DOCUMENTS 4,184,952  1/1980  Stewart ........................... 210/781
4,401,575  8/1983  Stewart et al. .................. 210/746

Primary Examiner—John Adee

[57] ABSTRACT

A process is provided for measuring the water and sediment content of a wet stream which is predominantly non-aqueous. The process requires removing a sample of the wet stream, extracting a dry stream sample from the wet stream sample, and comparing the dielectric constants of the wet and dry streams. Leakage of any of the wet stream sample into the dry stream sample will adversely affect the comparison of dielectric constants. Accordingly, periodically the apparatus used for the process is checked for leakage by blocking conduits carrying the dry stream sample to a holding chamber.

8 Claims, 1 Drawing Figure

LEAK DETECTION

BACKGROUND OF THE INVENTION

A device for measurement of basic sediment and water (BS&W) in a predominantly non-aqueous stream (e.g., pipeline crude oil), is disclosed in U.S. Pat. No. 4,184,952. This device is an improvement on capacitance type instruments of the art which are dependent upon the extent to which the intrinsic dielectric constant of the subject fluid varies with time. The gravity and physical composition of crude oil are two factors which determine its intrinsic dielectric constant. If one or both of these properties should vary, instruments measure the accompanying change in the dielectric constant as percent BS&W. This yields an inaccurate measurement of BS&W because instruments must be initially set to read zero BS&W as the intrinsic dielectric constant of the fluid. The capacitance type instruments of the prior art have no means for automatically correcting the zero BS&W setting to compensate for periodic variations in the oil properties mentioned. By comparison, the device of U.S. Pat. No. 4,184,952 provides for automatic compensation of BS&W measurements by producing a clean, dry sample of the line fluid for measurement of its intrinsic dielectric constant. In this way, the true BS&W content of the fluid is measured by finding the difference between the dielectric constants of the wet and dry streams.

While the improvement over the prior art represented by the invention of U.S. Pat. No. 4,184,952 is substantial, another improvement was made subsequently which even further increased the efficiency and accuracy of this device for BS&W measurement. Thus, it was discovered that seals between the wet oil and dry oil chambers of the device occasionally leak after extended usage. In view of the extreme sensitivity of this device, any leakage, however small, can measurably reduce the accuracy of readings. Accordingly, the invention of U.S. Pat. No. 4,401,575 substantially eliminated the possibility of any leakage from the wet oil chamber to the dry oil chamber.

Yet another improvement has now been made in this device for BS&W measurement. Thus, in view of the extreme sensitivity of the device to any minute leakage, it is desirable to be able to periodically check the device for leakage. Accordingly, the present invention provides a method and apparatus for checking the device for leakage which is reliable and which can be easily and readily installed.

SUMMARY OF THE INVENTION

Figure 1:
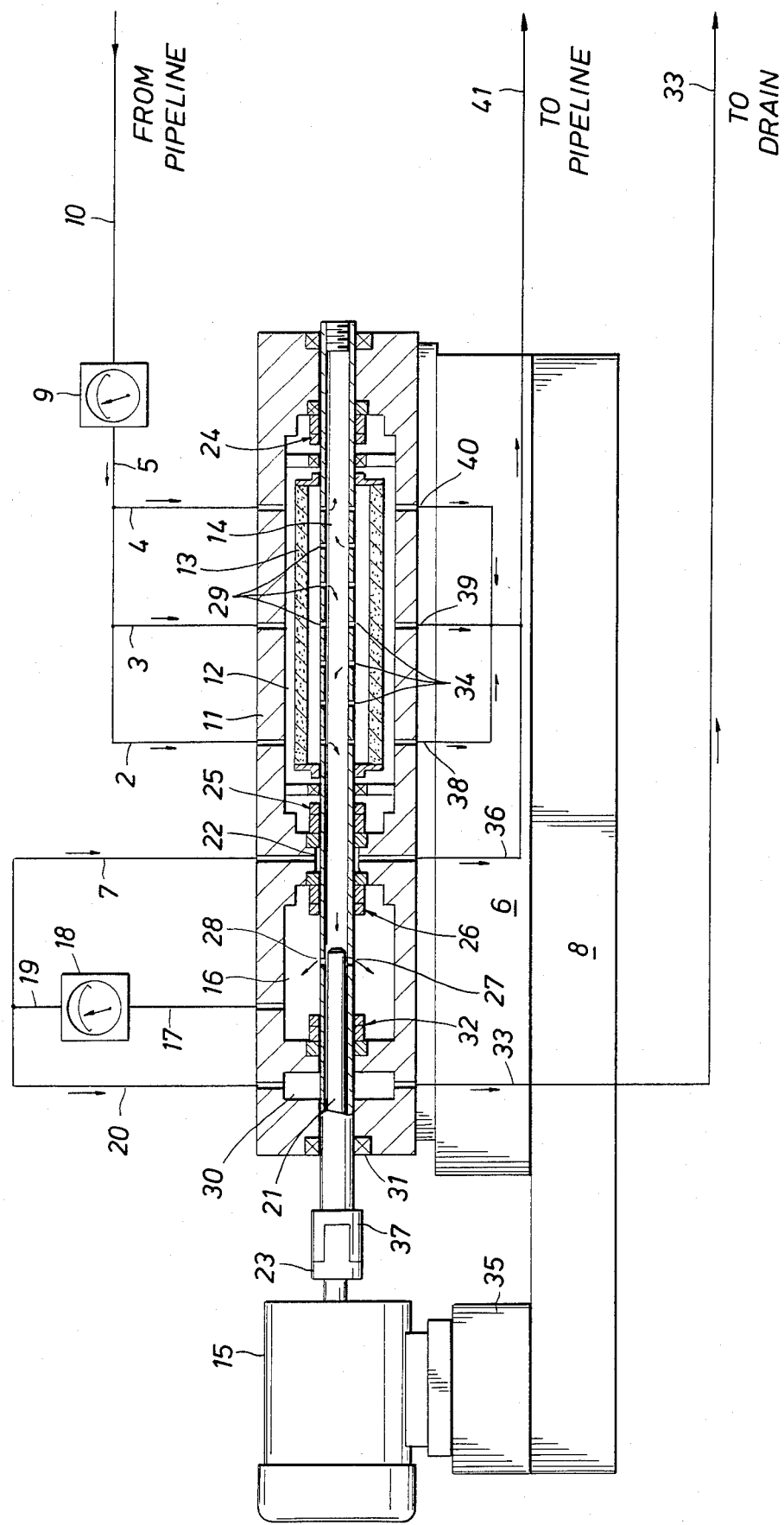
FIG. 1 schematically shows the flow paths of various streams within the apparatus of the invention.

The present invention pertains to a process and apparatus for checking for leaks between wet oil and dry oil chambers of a device for measuring basic sediment and/or water in a stream, particularly crude oil. More particularly, the process and apparatus utilize means for periodically blocking a passageway between the wet oil and dry oil chambers which normally carries dry oil during operation of the apparatus. Once flow is blocked, the dry chamber is then checked for leaks of wet oil from the wet oil chamber.

Specifically, the present invention provides a process and apparatus for measuring the water and sediment content of a wet stream which is predominantly non-aqueous, by removing a sample of the wet stream, admitting the wet stream sample to an outer chamber containing an inner chamber having a wall formed of a filter, rotating the inner chamber while pressuring the wet stream sample from the outer chamber into the inner chamber whereby sediment is filtered from the wet stream sample passing into the inner chamber and centrifugal force in the inner chamber forces water in the wet stream sample to remain or return to the outer chamber and thereby form a dry sample stream, passing the dry sample stream axially from the inner chamber to an aligned chamber which is separated and sealed from the outer chamber, periodically blocking the axial passage of the dry stream sample to the aligned chamber, and checking the aligned chamber for leakage from the outer chamber. Preferably, the blocking is effected by inserting a flow blocking rod into an axial passageway which carries the dry stream sample to the aligned chamber. More preferably, the rod is extended into the axial passageway up to a distance sufficient to block fluid flow ports from the passageway into the aligned chamber.

DESCRIPTION OF THE PREFERRED EMBODIMENTS

In accordance with the present invention, a process and apparatus are provided for checking the water/oil emulsion separator described in U.S. Pat. Nos. 4,184,952 and 4,401,575 for leakage of wet oil in one part of the separator into dry oil in another part of the separator. The invention of U.S. Pat. No. 4,401,575 is particularly concerned with seals which separate a centrifugal filter such as shown in U.S. Pat. No. 4,184,952 from other chambers in the apparatus which enclose wet and dry streams. In accordance with the invention of U.S. Pat. No. 4,401,575, the dry stream is employed as a flush which (1) cools the seals, (2) prevents any wax or polymer buildup resulting from minute leakage and (3) reduces the loading on the seal faces by minimizing the differential pressure across the faces. The present invention in effect takes the improvement of U.S. Pat. No. 4,401,575 one step further. Thus, not only is it desirable to prevent leaks from occurring, but it is also desirable to provide assurance that leakage in fact is not occurring, however remote the possibility.

In addition, the present invention makes other modifications of the original apparatus as shown in U.S. Pat. Nos. 4,184,952 and 4,401,575, as evident from the drawings hereof. Thus, the original apparatus included a cylindrical filter mounted on a hollow shaft rotating in a cylindrical chamber that is flanked on both ends by dry oil chambers. The hollow shaft delivers dry oil from the central chamber, which is separated from the outer chambers by double mechanical seals on each end. Including the seals on the extreme outer ends, the original apparatus contains six mechanical seals. The length of the shaft is such that two inner bearings are needed in addition to the end bearings. The bearings run in dirty crude oil and require periodic replacement by disassembling the apparatus. In order to eliminate the inner bearings, stiffening the shaft was required. This was effected by shortening the shaft. To shorten the shaft, one of the dry oil chambers was eliminated, and optionally the double seal between the remaining chamber and the wet oil chamber may be reduced to a single seal. These changes reduce cost of the apparatus by one third and reduce its energy consumption by one third, although the improved apparatus contains a full size filter element, runs smoothly, and produces dry oil at the same rate as the original apparatus.

A sectional view of the present invention is provided in FIG. 1 with flow streams shown schematically. Crude oil or other fluid containing a small amount of water is taken from a pipeline or other storage or transport via line 10 and passed through a wet oil capacitance measurement cell 9, and then via line 5, which is split into lines 2-4, through a housing 11 supported by structures 6 and 8, and then into wet oil chamber 12. Cell 9 determines the capacitance of the wet oil. From chamber 12, the wet oil is forced through filter 13 and into hollow drive shaft 14. Hollow drive shaft 14 and filter 13 are spun by a motor or other drive means 15 mounted on support 35. While the present invention is not limited to the following theory, it appears that the resulting centrifugal force substantially prevents the water and sediment capable of otherwise passing through filter 13, from entering hollow shaft 14, and any water or sediment that may enter shaft 14 is forced outwardly back into chamber 12. Dry fluid in hollow shaft 14 passes outwardly into dry oil chamber 16. Dry oil from chamber 16 then is passed via line 17 through a dry oil capacitance measurement cell 18 which determines the capacitance of the dry oil. As above noted, comparison of the capacitance of the dry oil with the capacitance of the wet oil facilitates determining the true BS&W content of the wet oil.

A portion or all of the dry oil stream 19 may be passed via line 7 into space 22 separating seals 25 and 26 which separate wet oil chamber 12 from dry oil chamber 16, or alternatively, seal 26 may not be present. An additional minor portion of the dry sample stream may be passed via lines 20 into space 30, which is adjacent outer seals 31 and 32. Space 30 is at atmospheric pressure, and accordingly, the dry oil therefrom is passed via lines 33 to drain or disposal. Dry oil from space 22 is passed via lines 36 along with wet oil from lines 38, 39 and 40 back to the pipeline or other storage or transport via line 41.

Plug or rod 21 is inserted into hollow shaft 14 by disconnecting clamps 23 and 37 from drive means 15, or alternatively, drive means 15 may be at the opposite end of the shaft. Preferably, the plug is inserted just past apertures 27 and 28 which permit dry oil to enter chamber 16. It is not necessary to insert rod 21 past apertures 29 and 34 in wet oil chamber 12. This then permits making a check of chamber 16 during operation of the apparatus to see if any leakage is occurring through seals 25 and 26.

While the present invention has been described principally in connection with a basic sediment and water instrument and in terms of crude oil and wet and dry streams of such crude oil, it will be apparent that the basic principles of the invention are adaptable to other processes and apparatus utilizing non-oil streams, where it is desirable to clean or flush seals between chambers containing different fluids.

What is claimed is:

1. A process for measuring the water and sediment content of a wet stream which is predominantly non-aqueous, comprising, removing a sample of the wet stream, admitting the wet stream sample to an outer chamber containing an inner chamber having a wall formed of a filter, rotating the inner chamber while pressuring the wet stream sample from the outer chamber into the inner chamber, whereby sediment is filtered from the wet stream sample passing into the inner chamber and centrifugal force in the inner chamber forces water and sediment in the wet stream sample to remain in the outer chamber and thereby form a dry sample stream, passing the dry sample stream axially from the inner chamber to an aligned chamber which is separated and sealed from the outer chamber, periodically blocking the axial passage of the dry stream sample to the aligned chamber, and checking the aligned chamber for leakage from the outer chamber.

2. The process of claim 1 wherein the blocking is effected by inserting a flow blocking rod into an axial passageway which carries the dry stream sample to the aligned chamber.

3. The process of claim 2 wherein the rod is extended into the axial passageway up to a distance sufficient to block fluid flow ports from the passageway into the aligned chamber.

4. The process of claim 1 wherein the wet stream is pipeline crude oil.

5. An apparatus for measuring the water and sediment content of a wet stream which is predominantly non-aqueous, comprising, means for removing a sample of the wet stream, means for admitting the wet stream sample to an outer chamber containing an inner chamber having a wall formed of a filter, means for rotating the inner chamber while pressuring the wet stream sample from the outer chamber into the inner chamber to form a dry sample stream, means for passing the dry sample stream axially from the inner chamber to an aligned chamber which is separated and sealed from the outer chamber, means for periodically blocking the axial passage of the dry stream sample to the aligned chamber, and means for checking the aligned chamber for leakage from the outer chamber.

6. The apparatus of claim 5 wherein the blocking means is a flow blocking rod insertable into an axial passageway which carries the dry stream sample to the aligned chamber.

7. The apparatus of claim 6 wherein the rod is extendable into the axial passageway up to a distance sufficient to block fluid flow from the passageway into the aligned chamber.

8. The apparatus of claim 5 wherein the wet stream is crude oil which is in a pipeline.

* * * * *